(12) United States Patent
Dirksen et al.

(10) Patent No.: US 12,004,902 B2
(45) Date of Patent: Jun. 11, 2024

(54) SYSTEMS AND METHODS FOR PERFORMING BI-PLANE IMAGING

(71) Applicant: KONINKLIJKE PHILIPS N.V., Eindhoven (NL)

(72) Inventors: Peter Dirksen, Hilversum (NL); Nico Maris Adriaan de Wild, Eindhoven (NL); Marc Godfriedus Marie Notten, Elsloo (NL); Christianus Martinus van Heesch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 417 days.

(21) Appl. No.: 17/270,004

(22) PCT Filed: Aug. 16, 2019

(86) PCT No.: PCT/EP2019/071987
§ 371 (c)(1),
(2) Date: Feb. 20, 2021

(87) PCT Pub. No.: WO2020/038835
PCT Pub. Date: Feb. 27, 2020

(65) Prior Publication Data
US 2021/0321981 A1    Oct. 21, 2021

(30) Foreign Application Priority Data
Aug. 21, 2018  (EP) ..................... 18189995

(51) Int. Cl.
*A61B 8/14*   (2006.01)
*A61B 8/00*   (2006.01)
(Continued)

(52) U.S. Cl.
CPC ............ *A61B 8/145* (2013.01); *A61B 8/4254* (2013.01); *A61B 8/4477* (2013.01);
(Continued)

(58) Field of Classification Search
CPC ..... A61B 8/145; A61B 8/4245; A61B 8/4254; A61B 8/4427; A61B 8/4444;
(Continued)

(56) References Cited

U.S. PATENT DOCUMENTS 5,957,850 A  9/1999  Marian, Jr. et al.
6,122,538 A  9/2000  Sliwa, Jr. et al.
(Continued)

FOREIGN PATENT DOCUMENTS

CN    202801811 U     3/2013
DE    102013216152 A1 *  2/2015   ........... A61B 8/4427
(Continued)

OTHER PUBLICATIONS

Translated copy of Foreign Takeshi JP 2008125692 A (Year: 2008).*
(Continued)

*Primary Examiner* — Katherine L Fernandez
*Assistant Examiner* — Brooke Lyn Klein

(57) ABSTRACT

The invention provides a handheld imaging device capable of performing biplane imaging, wherein a first image plane or a second imaging plane (having different orientations) may be selected for image capture based on a motion characteristic of the device as determined by a sensor.

10 Claims, 5 Drawing Sheets

(51) Int. Cl.
    *B06B 1/02*    (2006.01)
    *B06B 1/06*    (2006.01)
    *G01P 15/00*   (2006.01)
    *G01S 15/89*   (2006.01)

(52) U.S. Cl.
    CPC .......... *A61B 8/4488* (2013.01); *A61B 8/4494* (2013.01); *A61B 8/54* (2013.01); *B06B 1/0292* (2013.01); *B06B 1/0622* (2013.01); *G01P 15/00* (2013.01); *G01S 15/8925* (2013.01)

(58) Field of Classification Search
    CPC ... A61B 8/4477; A61B 8/4483; A61B 8/4488; A61B 8/4494; A61B 8/463; A61B 8/467; A61B 8/483; A61B 8/5246; A61B 8/54; G01S 15/8925; G01S 7/52074
    See application file for complete search history.

(56) References Cited

U.S. PATENT DOCUMENTS

| | | | | |
|---|---|---|---|---|
| 6,338,716 | B1* | 1/2002 | Hossack | G01S 7/5208 600/459 |
| 2003/0060710 | A1 | 3/2003 | Salgo et al. | |
| 2005/0256407 | A1 | 11/2005 | Hamada | |
| 2007/0078340 | A1 | 4/2007 | Wilcox et al. | |
| 2008/0294052 | A1 | 11/2008 | Wilser et al. | |
| 2009/0043209 | A1* | 2/2009 | Hirama | A61B 8/483 600/459 |
| 2011/0320143 | A1 | 12/2011 | Hopkins | |
| 2015/0257733 | A1 | 9/2015 | Corbett, III et al. | |
| 2016/0310992 | A1* | 10/2016 | Van Rens | A61B 8/4494 |
| 2017/0367685 | A1* | 12/2017 | Zou | G06F 18/22 |

FOREIGN PATENT DOCUMENTS

| | | | |
|---|---|---|---|
| JP | H08257028 A | | 10/1996 |
| JP | 2008125692 A | * | 6/2008 |
| WO | 9732277 A1 | | 9/1997 |
| WO | 2017200515 A1 | | 11/2017 |
| WO | 2018094118 A1 | | 5/2018 |

OTHER PUBLICATIONS

Huang, "a Review on Real-Time 3D Ultrasound Imaging Technology", BioMed Research International (Year: 2017).*
McGhie, et al., "Contributions of Simultaneous Multiplane Echocardiographic Imaging in Daily Clinical Practice", Echocardiography, vol. 31, No. 2, Oct. 18, 2013, pp. 245-254.
Shaulov, et al., "Biplane Phased Array for Ultrasonic Medical Imaging", IEEE 1988 Ultrasonics Symposium Proceedings, Jan. 1, 1988, pp. 635-638.
International Search Report and Written Opinion for International Application No. PCT/EP2019/071987, filed Aug. 16, 2019, 15 pages.

* cited by examiner

SYSTEMS AND METHODS FOR PERFORMING BI-PLANE IMAGING

RELATED APPLICATIONS

This application is the U.S. National Phase application under 35 U.S.C. § 371 of International Application No. PCT/EP2019/071987, filed on Aug. 16, 2019, which claims the benefit and priority to European Application No. 18189995.6, filed Aug. 21, 2018, which is incorporated by referenced in its entirety.

FIELD OF THE INVENTION

This invention relates to the field of ultrasound imaging, and in particular to the field of bi-plane ultrasound imaging.

BACKGROUND OF THE INVENTION

In typical ultrasound imaging systems, the ultrasound probe is capable of capturing image data in a single plane of acquisition. In order to alter the plane of acquisition, the technician is required to manually rotate the probe to the desired field of view.

In systems where the ultrasound probe is capable of bi-plane imaging, the alternation between the image acquisition planes is commonly performed using a switch. This requires the technician to manually provide an input to the ultrasound system, which may be not be possible in certain imaging scenarios. Further, the need to manually provide an input draws the attention of the technician away from the imaging screen and may result in the ultrasound probe shifting position and the technician losing their place in the imaging process.

There is therefore a need for a means of adjusting the image acquisition plane of a bi-plane imaging system in a more convenient manner, without requiring significant additional hardware.

Document US 2015/257733 discloses a wearable ultrasound system comprising an ultrasound probe, a proximal wearable component electrically interconnected with said ultrasound probe adapted to be wearable on the hand of a user.

Document US 2011/320143 discloses an ultrasound probe including an accelerometer configured to detect the movement of the probe.

Document Jackie S. McGhie et al. discloses a 2D/3D matrix transducer introducing an image modality called simultaneous multi-pane imaging.

Document US 2007/078340 discloses a method and system for providing an operational command signal to a workstation of an imaging system.

Document US 2008/294052 discloses an ultrasonic imaging tube having a first transducer array and a second transducer array that are at a non-zero angle to each other about the longitudinal axis of the tube.

SUMMARY OF THE INVENTION

The invention is defined by the claims.

According to examples in accordance with an aspect of the invention, there is provided a handheld imaging device, wherein the device comprises:

a bi-plane imaging system comprising a first ultrasonic transducer array and adapted to acquire image data in a first imaging plane having a first orientation and a second imaging plane having a second orientation by way of said first ultrasonic transducer array, wherein the first orientation is different from the second orientation;

a sensor adapted to detect a motion of the imaging device; and a controller, wherein, during acquisition of the image data, the controller is adapted to:
if the sensor detects the motion of the imaging device with a first characteristic, select the first imaging plane; or
if the sensor detects the motion of the imaging device with a second characteristic different from the first characteristic, select the second imaging plane.

The bi-plane imaging system is capable of capturing images along two different planes. The controller acts to automatically select which plane is used to capture the image based on the motion of the probe detected by the sensor.

For example, if the device is moved along the length of a user's arm, the imaging system may be selected to capture a cross-sectional image of the arm, which may be used in vessel diameter assessment. Alternatively, if the device is moved across the width of a user's arm, the imaging system may be selected to capture a longitudinal image (in this case orthogonal to the cross sectional image), which may be used in flow assessment.

In this way, the user may select the desired imaging plane by simply altering the motion of the handheld imaging device.

The first ultrasonic transducer array may be operated in a bi-plane mode so as to generate images from two different imaging planes.

In a further embodiment, the bi-plane imaging system further comprises a second ultrasonic transducer array.

During normal operation, the first ultrasonic transducer array will generate an image in the first imaging plane, which is based on the orientation of the first ultrasonic transducer array.

By providing the handheld imaging device with a second ultrasonic transducer array, it is possible to generate an image in the second imaging plane in a simple manner. In this case, the controller may simply activate the first ultrasonic transducer array and deactivate the second ultrasonic transducer array, or vice versa, according to the detected motion of the probe in order to change the imaging plane of the handheld imaging device.

In a further embodiment, the first ultrasonic transducer array is adapted to acquire image data in the first imaging plane and the second ultrasonic transducer array is adapted to acquire image data in the second imaging plane, wherein the first imaging plane is orthogonal to the second imaging plane.

In this way, the first imaging plane and the second imaging plane may be orthogonal to each other. By way of example, this may be used to collect both a cross sectional image of a blood vessel in the first imaging plane and a blood flow velocity calculation along the length of the vessel in the second imaging plane.

In another embodiment, the first and second ultrasonic transducer arrays are arranged in a Fishbone pattern.

By arranging the ultrasonic transducer arrays in a Fishbone pattern, the first imaging plane and second imaging plane may be made to be orthogonal to each other, whilst also reducing the physical space required to house the first and second ultrasonic transducer arrays. Thus, the physical size of the bi-plane imaging system may be reduced.

In an arrangement, the bi-plane imaging system comprises a CMUT.

In an embodiment, the sensor comprises an accelerometer.

In this way, a directional assessment of the motion of the handheld imaging device may be performed based on the acceleration of the device. Further, the accelerometer may also be used in assessing the tilt of the device.

In an arrangement, the sensor comprises an optical sensor.

In this way, it is possible to assess the translation and rotation of the device.

In an embodiment, the first characteristic and the second characteristic of the motion of the imaging device comprises a translation.

By triggering the change in imaging plane based on a translation, the user may simply switch between the imaging planes by moving the device in different directions.

In a further embodiment, the first characteristic translation is orthogonal to the second characteristic translation.

Defining the first characteristic translation as orthogonal to the second characteristic translation provides a clear distinction between the motions required to alter the imaging plane captured by the handheld imaging device, thereby increasing the ease of use of the device for the user.

In an arrangement, the first characteristic and the second characteristic of the motion of the device comprises a two-dimensional rotation.

In this way, it is possible to better track the location of the device in each set of image data.

In an embodiment, the first characteristic and the second characteristic of the motion comprises a three-dimensional orientation.

In this way, it is possible to detect the angle of the handheld imaging device relative to the normal of the imaging surface. In other words, the three-dimensional orientation may be used to assess by how much the device is tilted relative to the imaging surface.

In this way, it is possible to monitor the location and orientation of the device in each set of image data.

According to examples in accordance with an aspect of the invention, there is provided an imaging system, the system comprising:
  a handheld imaging device as defined above;
  an image processor, adapted to generate an image based on the acquired image data; and
  a display for displaying the image.

According to examples in accordance with an aspect of the invention, there is provided an imaging method, the method comprising, during the acquisition of image data:
  detecting the motion of an imaging device; and
  if the detected motion of the imaging device is in a first direction, acquiring image data in a first imaging plane having a first orientation by way of a first ultrasonic transducer array; or
  if the detected motion of the imaging device is in a second direction different from the first direction, acquiring image data in a second image plane having a second orientation by way of a first ultrasonic transducer array, wherein the first orientation is different from the second orientation.

According to examples in accordance with an aspect of the invention, there is provided a computer program comprising computer program code means which is adapted, when said computer program is run on a computer, to implement the method described above.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
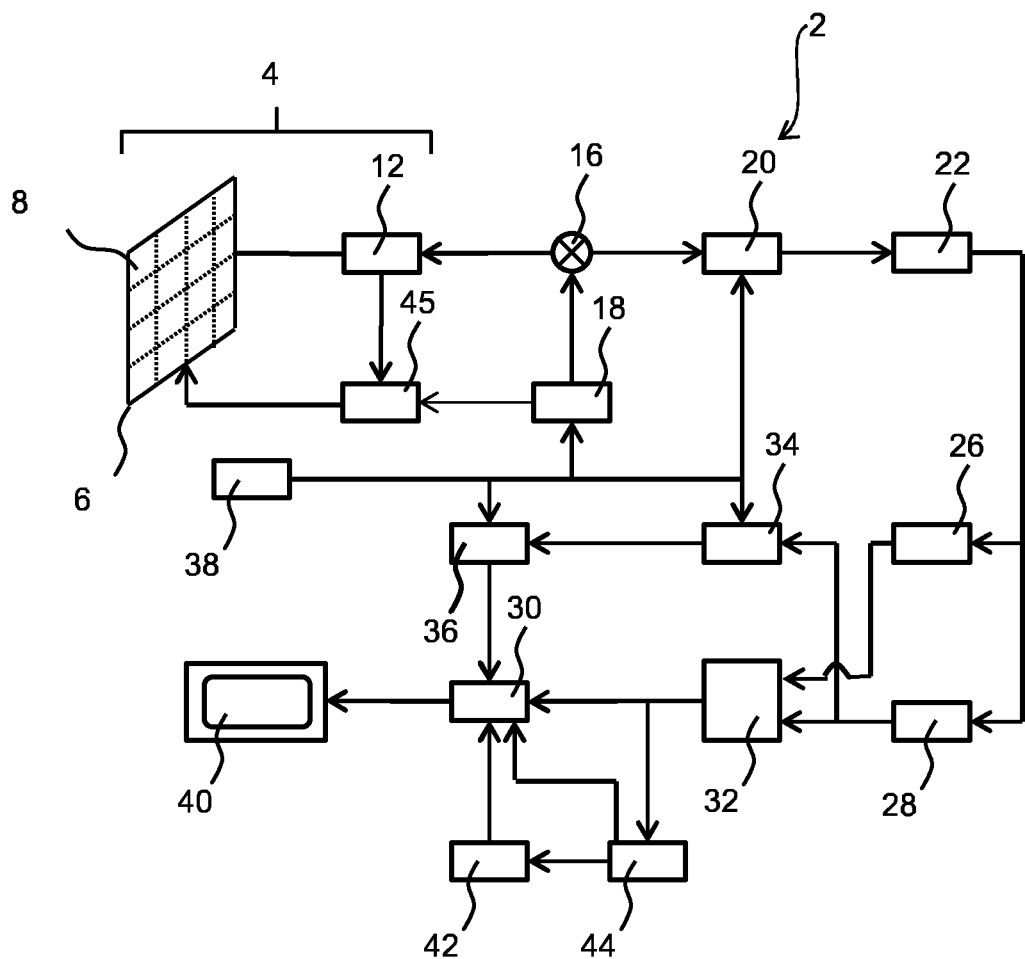
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a handheld imaging device capable of performing bi-plane imaging, wherein a first image plane or a second imaging plane (having different orientations) may be selected for image capture based on a motion characteristic of the device as determined by a sensor.

As the handheld imaging device may be employed as an ultrasound probe in an ultrasound imaging system, the general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figures 2A, 2B:
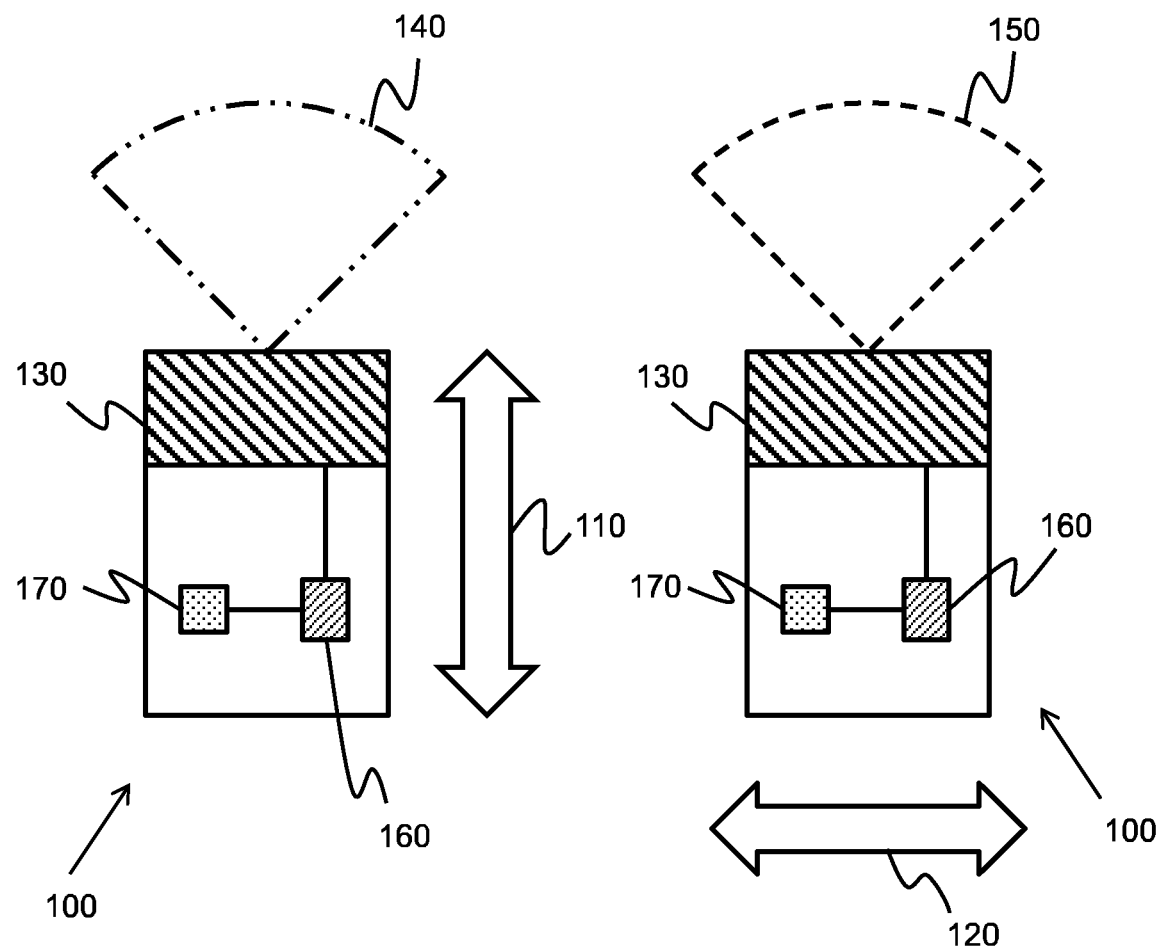
FIG. 2 shows a schematic representation of the handheld imaging device.

FIGS. 2a and 2b show a handheld imaging device 100 undergoing a first motion characteristic 110 and a second motion characteristic 120, respectively.

In this example, the first motion characteristic 110 and the second motion characteristic 120 are translations, wherein the first characteristic translation is orthogonal to the second characteristic translation.

The handheld imaging device comprises a bi-plane imaging system 130 adapted to acquire image data in a first imaging plane 140 having a first orientation and a second imaging plane 150 having a second orientation, wherein the first orientation is different from the second orientation by way of a first ultrasonic transducer array.

The selection of which imaging plane is captured by the bi-plane imaging system 130 is controlled by a controller 160 during acquisition of image data based on the output of a sensor 170, wherein the sensor is adapted to capture a motion of the device.

In the examples shown in FIGS. 2a and 2b, the controller 160 selects the first imaging plane 140 of the bi-plane imaging system 130 when the sensor 170 detects a motion of the device having a first characteristic 110. Similarly, the controller selects the second imaging plane 150 of the bi-plane imaging system when the sensor detects a motion of the device having a second characteristic 120.

In other words, when the sensor detects a motion in line with the normal of the bi-plane imaging system i.e. forwards and backwards, the first imaging plane may be selected. When the sensor detects a motion perpendicular to the normal of the bi-plane imaging system i.e. side to side, the second imaging plane may be selected.

The sensor 170 of the handheld imaging device may comprise any sensor suitable for detecting motion.

In an example, the sensor may comprise an optical sensor, which monitors the motion of the device through optical tracking. Optical tracking may use a variety of cameras in order to track the motion of the device, such as: a visible frequency range camera; an infrared camera; a stereo camera; a depth camera; or any other suitable camera.

Alternatively, the optical tracking may be performed by an LED coupled with a light detector, such as an array of photodiodes, to detect movement relative to a surface.

An optical sensor may be used to track the translation and/or 2D rotation, as described with reference to FIG. 3 below, of the handheld imaging device.

In a further example, the sensor may comprise an accelerometer, which may be used to detect an acceleration of the handheld imaging device in a given direction when it is moved by a user. In addition, the accelerometer may be used to determine a 3D orientation (tilt) of the handheld imaging device, as described below with reference to FIG. 4.

The handheld imaging device may undergo a calibration stage before the imaging process begins in order to establish the first characteristic and the second characteristic of the motion of the probe. For example, the user may indicate to the handheld imaging device that a given motion should be recognized as the first characteristic, such as the forwards and backwards motion 110 shown in FIG. 2a, whilst moving the device in said given motion. The user may then also indicate to the handheld imaging system that a different given motion should be recognized as the second characteristic, such as the side to side motion 120 shown in FIG. 2b, whilst moving the device in said different given motion.

The user may initiate this calibration process by way of a suitable user input. Alternatively, the handheld imaging device may request the user perform a calibration process, such as the one described above, before initiating the imaging process. The calibration process may be performed for each use of the handheld imaging device, or the device may store calibration data for use in subsequent imaging processes.

Alternatively, the user may initiate the imaging process and the first image, and its associated location and/or orientation, may be taken as a reference point for establishing the first characteristic and second characteristic motion of the device for acquiring a first and second imaging plane.

The ultrasound probe 4 may be a 3D ultrasound imaging probe, comprising an electronically steered 2D array of transducer elements, and adapted to capture 3D ultrasound images. The 3D ultrasound images may be acquired by acquiring a plurality of 2D ultrasound images, each separated by a given displacement as dictated by the electronic steering of the ultrasound beam, and combining the acquired 2D ultrasound images to form the final 3D ultrasound image.

In this case, the first and second imaging planes may be acquired from any available orientation within the volume of the 3D ultrasound image. As described above, the first imaging plane having a first orientation and the second imaging plane having the second orientation may be acquired according to a sensed motion of the imaging probe having a first or second characteristic, respectively.

In an example, the first and second orientations of the first and second imaging planes may be fixed at a given location and orientation within the volume of the 3D ultrasound image. This may be used in situations where precise measurements of a given anatomical feature are required. In practice, the user may hold the probe in a given location to maintain a view of a desired volume of the subject. The location and orientation of the first and second imaging planes may then be defined according to the current application of the imaging process. The user may then swap between the acquisition of the first imaging plane or the second imaging plane by way of a predefined motion characteristic, such as a rotation of the probe. As the imaged area will remain largely the same, and the rotation of the probe may be accounted for, the imaging data acquired from the first and second imaging plane may remain consistent during the acquisition process.

In a further example, the first and second orientations may be altered according to a motion characteristic of the probe. For example, the first and second imaging planes may be fixed in a first and second orientation relative to the ultrasound imaging probe, meaning that the first and second imaging planes will follow any changes in the rotation or orientation of the imaging probe. In this case, the selection of acquiring the first and second imaging plane may be performed based only on a translation motion characteristic, such as by moving the probe in a first direction to acquire the first imaging plane and a second direction, orthogonal to the first without rotating the probe, to acquire the second imaging plane.

In addition, for a 3D ultrasound image, the number of imaging planes may be increased. For example, there may be a third imaging plane having a third orientation which may be acquired according to a motion of the probe having a third characteristic. This may be performed for any number of additional imaging planes according to the application.

Figure 3:
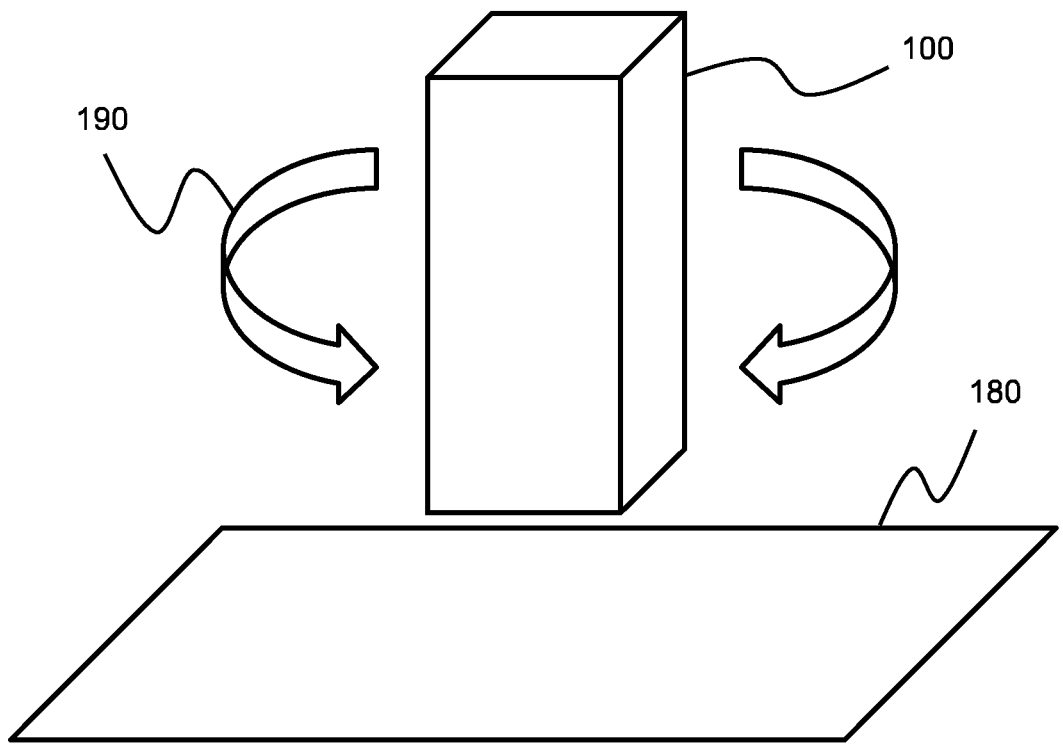
FIG. 3 demonstrates a 2D rotation of the handheld imaging device.

FIG. 3 shows a handheld imaging device 100 located above an imaging surface 180, such as a user's skin. In this case, the motion of the probe is a 2D rotation 190 about the normal of the imaging surface. For example, the first characteristic may be a clockwise rotation about the normal to the imaging surface and the second characteristic may be an anti-clockwise rotation.

Figure 4:
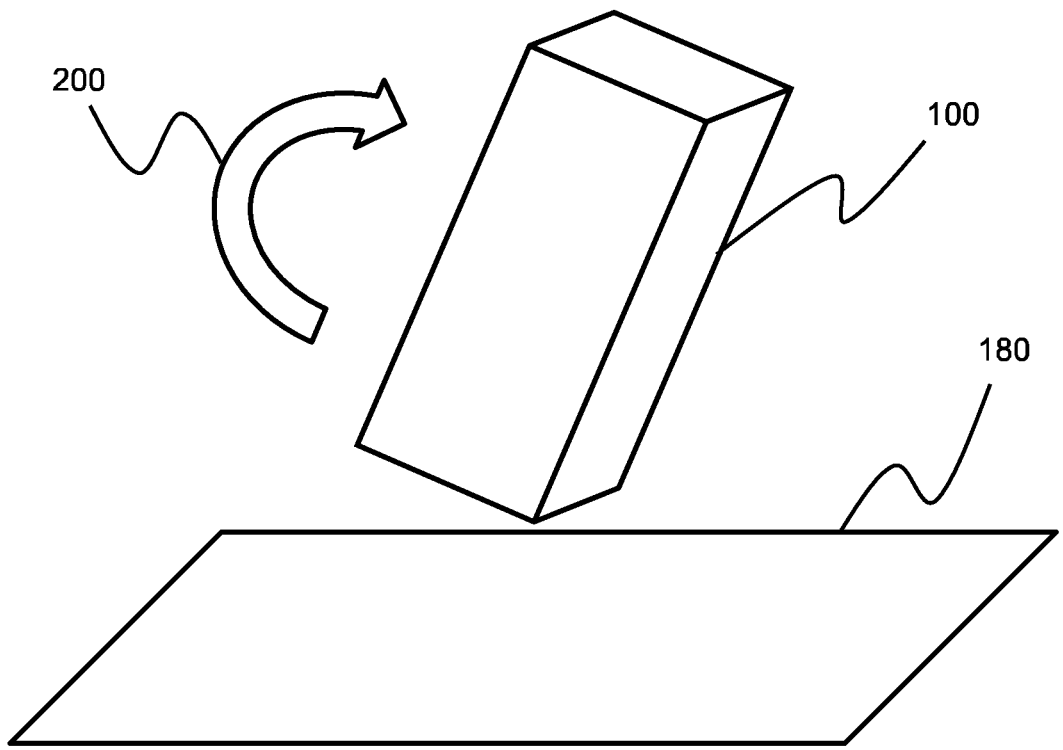
FIG. 4 demonstrates a 3D orientation of the handheld imaging device.

FIG. 4 shows a further representation of a handheld imaging device 100 located above an imaging surface 180. In this case the motion of the probe is a 3D orientation 200 relative to the normal of the imaging surface. In other words, the first and second characteristics of the motion of the device may be a tilt of the handheld imaging device.

Figure 5:
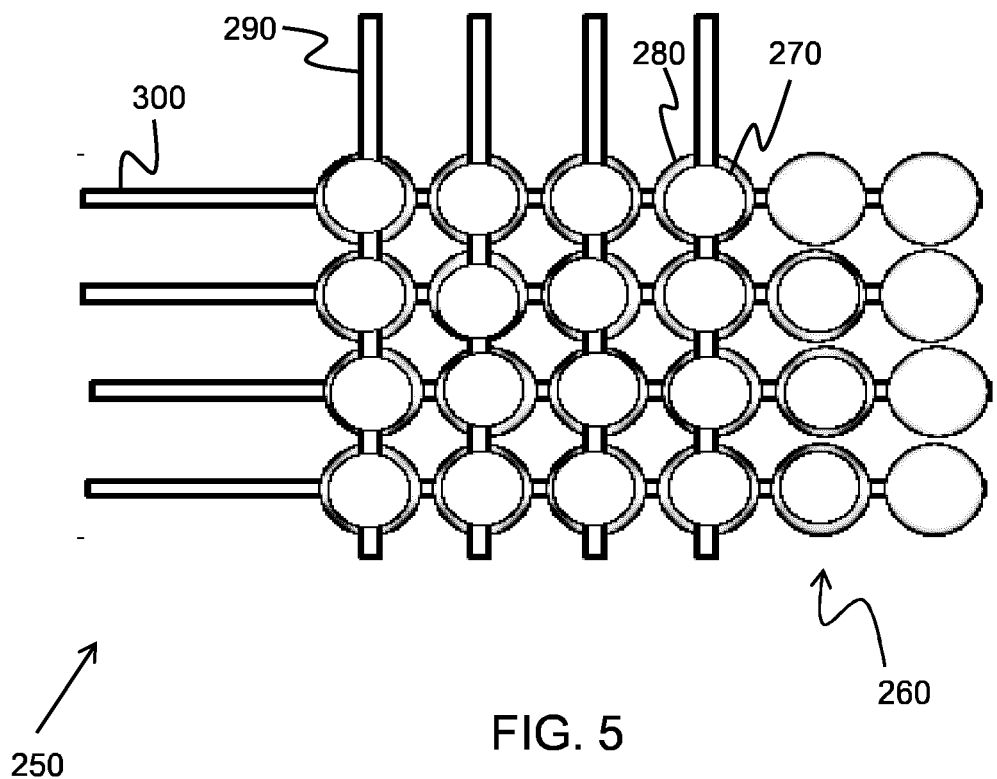
FIG. 5 shows a schematic representation of the first ultrasonic imaging array comprising CMUTs.

FIG. 5 shows a first ultrasonic transducer array 250 wherein the transducers are CMUTs 260, which comprise and upper electrode 270 and a lower electrode 280. The operation of the first transducer array as a bi-plane imaging system will now be described.

As stated, a CMUT comprises an upper and lower electrode. These electrodes are separated by a cavity, wherein the bottom electrode is fixed at one side of the cavity and the upper electrode is suspended at the opposite side of the cavity by way of a flexible membrane. When a bias voltage is supplied to one of the electrodes, they are brought together and the flexible membrane enters a depressed state. In this state, the membrane can be made to vibrate at ultrasonic frequencies by supplying a radio frequency (RF) signal to the electrode without the bias voltage.

As described above, a transducer array may be operated in a line-by-line manner in order to build up and ultrasound image. A 2D array possesses two directions in which a line-by-line imaging sequence may progress, meaning that it is possible to perform bi-plane imaging using a single array.

The CMUTs 260 of first ultrasonic transducer array 250 may be connected to a first conductor 290 and a second conductor 300. In this example, the first conductor is connected to the upper electrode 270 and the second conductor is connected to the lower electrode. Each transducer connected by a common first or second conductor define a line of the line-by-line imaging process.

When capturing the first imaging plane 140, the bias voltage may be provided to the lower electrodes 280 of the CMUTs 260 by way of the second conductors 300. The RF signal may then be provided to the upper electrodes 270 of the CMUTs by way of the first conductors 290 in a line-by-line basis.

Similarly, when capturing the second imaging plane 150, the bias voltage may be provided to the upper electrodes 270 of the CMUTs 260 by way of the first conductors 290. The RF signal may then be provided to the lower electrodes 280 of the CMUTS by way of the second conductors 300 in a line-by-line basis.

In the example shown in FIG. 5, the first and second imaging planes will be orthogonal to each other; however, it is possible to arrange the first ultrasonic transducer array in such as way as to generate first and second imaging planes having orientations other than orthogonal to each other.

Figures 6A, 6B:
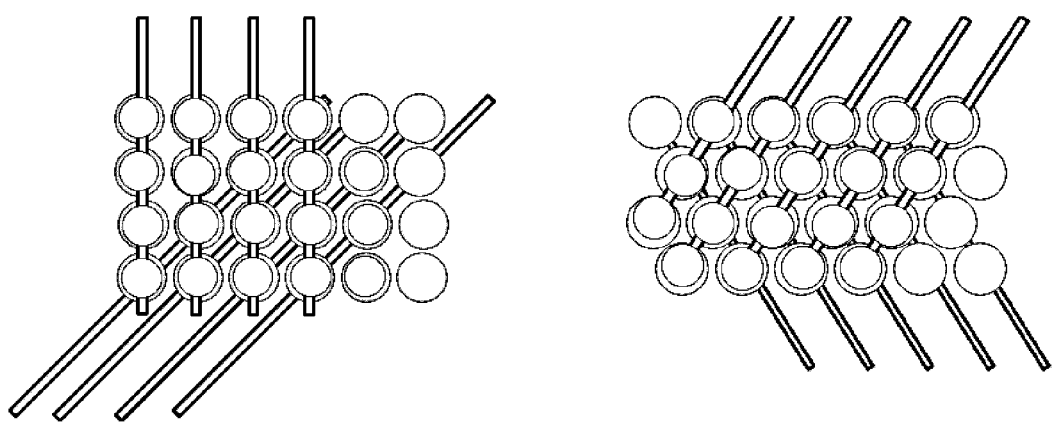
FIGS. 6a and 6b show alternative arrangements of the first ultrasonic imaging array shown in FIG. 5.

FIGS. 6a and 6b show examples of a first ultrasonic transducer array capable of producing imaging planes at 45° and 60° to each other, respectively.

Figure 7:
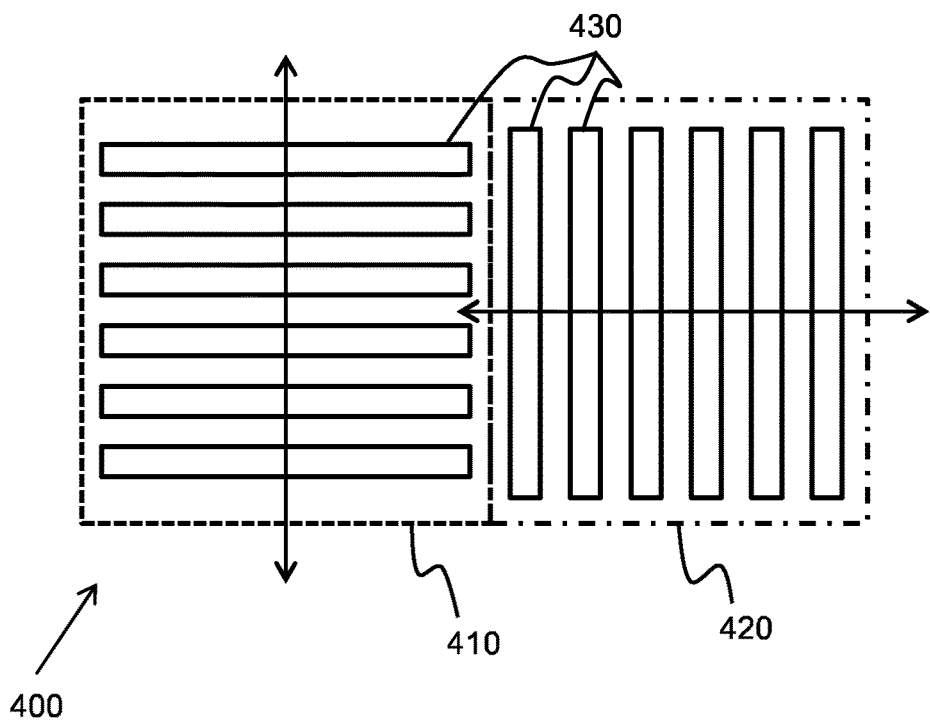
FIG. 7 shows a schematic representation of a first and second ultrasonic transducer array.

FIG. 7 shows a bi-plane imaging system 400 comprising a first ultrasonic transducer array 410 and a second ultrasonic transducer array 420, each comprising a plurality of lines of transducers 430.

When the sensor of the handheld imaging device detects a motion of the device with a first characteristic, the first ultrasonic transducer array may be activated in order to acquire a first imaging plane. Similarly, when the sensor of the handheld imaging device detects a motion of the device with a second characteristic, the second ultrasonic transducer array may be activated in order to acquire a second imaging plane.

The possible directions of the line-by-line imaging acquisition propagation direction are shown by the arrows.

In this example, the propagation direction of the line-by-line image acquisition of the first ultrasonic transducer array is orthogonal to the propagation direction of the second ultrasonic transducer array, meaning that the first and second imaging planes are also orthogonal to one another; however, they may also be arranged at any given angle to produce the desired imaging planes for the current operation of the device.

Figure 8:
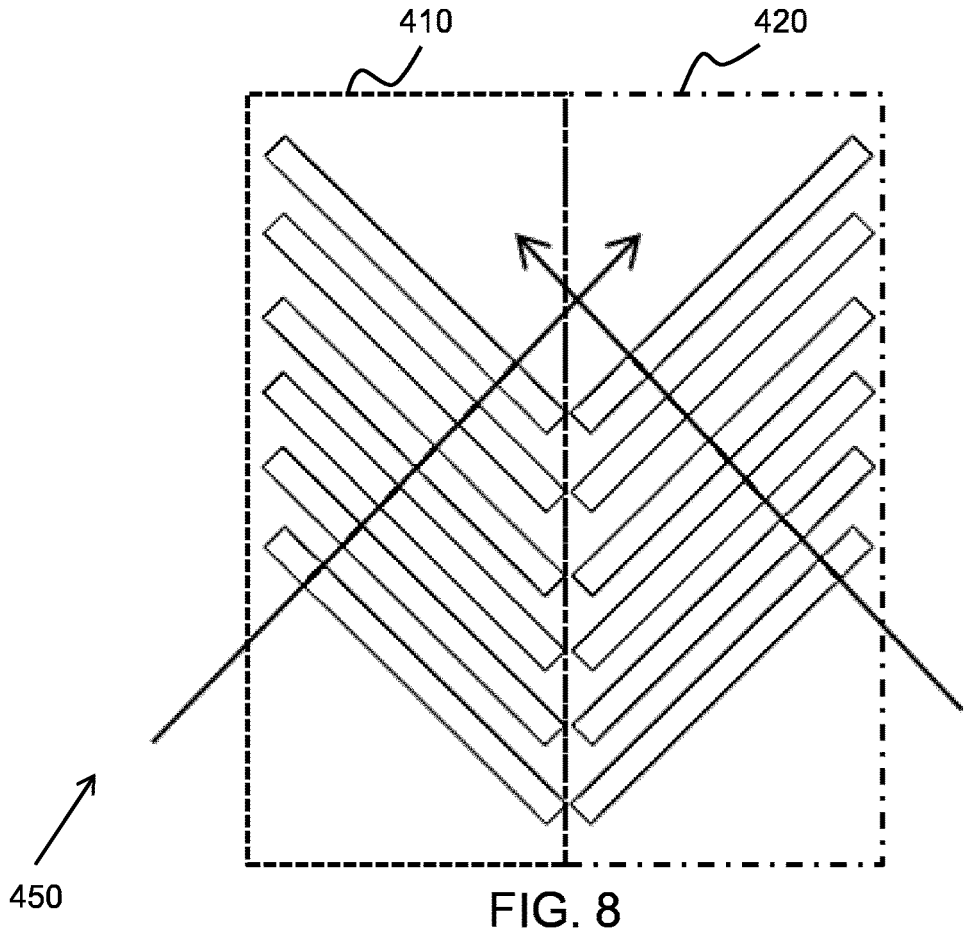
FIG. 8 shows a schematic representation of a first and second ultrasonic transducer array arranged in a Fishbone pattern.

FIG. 8 shows a further arrangement 450 of the first and second ultrasonic transducer arrays, wherein the lines of transducers are arranged in a Fishbone pattern.

Once again, the Fishbone pattern shown in FIG. 8 will produce orthogonal first and second imaging planes; however, the angle between the transducer lines of the first and second ultrasound imaging arrays may be altered to meet any desired angle between the first and second imaging planes.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A handheld imaging device, comprising:
  a bi-plane imaging system that comprises a first ultrasonic transducer array, wherein the bi-plane imaging system is adapted to acquire image data (i) in a first imaging plane having a first orientation and (ii) in a second imaging plane having a second orientation, wherein the first orientation is different from the second orientation;
  a sensor adapted to detect a motion of the handheld imaging device, wherein the sensor is adapted to detect at least motion of the handheld imaging device having a first characteristic and motion of the handheld imaging device having a second characteristic different from the first characteristic; and
  a controller adapted to trigger a change in imaging plane of the bi-plane imaging system during acquisition of the image data by selecting (i) the first imaging plane for acquiring the image data in response to the sensor detecting the motion having the first characteristic, and (ii) the second imaging plane for acquiring the image data in response to the sensor detecting the motion having the second characteristic, wherein the first characteristic and the second characteristic of the motion of the imaging device comprise a translation, and further wherein the first characteristic translation is orthogonal to the second characteristic translation.

2. The handheld imaging device of claim 1, wherein the bi-plane imaging system further comprises a second ultrasonic transducer array.

3. The handheld imaging device of claim 1, wherein the first transducer array comprises a capacitive micromachined ultrasonic transducer (CMUT).

4. The handheld imaging device of claim 1, wherein the sensor comprises an accelerometer.

5. The handheld imaging device of claim 1, wherein the sensor comprises an optical sensor.

6. An imaging system, comprising:
   the handheld imaging device of claim 1;
   an image processor, adapted to generate an image based on the acquired image data; and
   a display for displaying the generated image.

7. The handheld imaging device of claim 2, wherein the first ultrasonic transducer array is adapted to acquire the image data in the first imaging plane and the second ultrasonic transducer array is adapted to acquire the image data in the second imaging plane, wherein the first imaging plane is orthogonal to the second imaging plane.

8. The handheld imaging device of claim 2, wherein the first and second ultrasonic transducer arrays are arranged in a Fishbone pattern.

9. An method for imaging during acquisition of image data with a handheld imaging device comprising a bi-plane imaging system, the method comprising:

detecting, via a sensor, a motion of the handheld imaging device having a first characteristic and a motion of the handheld imaging device having a second characteristic different from the first wherein the bi-plane imaging system comprises a first ultrasonic transducer array, and wherein the imaging device is adapted to acquire the image data (i) in a first imaging plane having a first orientation and (ii) in a second imaging plane having a second orientation, wherein the first orientation is different from the second orientation; and triggering a change in imaging plane during acquisition of the image data, via a controller, by selecting (i) the first imaging plane for acquiring the image data via the first ultrasonic transducer array in response to the sensor detecting the motion having the first characteristic, and (ii) the second imaging plane for acquiring image data via the first ultrasonic transducer array in response to the sensor detecting the motion having the second characteristic, wherein the first characteristic and the second characteristic of the motion of the handheld imaging device comprise a translation, and further wherein the first characteristic translation is orthogonal to the second characteristic translation.

10. A non-transitory computer readable medium embodied with a computer program comprising computer program code which is adapted, when said computer program is run on a computer, to implement the method of claim 9.

* * * * *